United States Patent
Chan et al.

(10) Patent No.: US 10,180,423 B2
(45) Date of Patent: Jan. 15, 2019

(54) MICROPILLAR ARRAYS FOR ASSAYING MYELINATION

(71) Applicant: The Regents of the University of California, Oakland, CA (US)

(72) Inventors: Jonah R. Chan, Burlingame, CA (US); Seonok Lee, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 269 days.

(21) Appl. No.: 14/649,826

(22) PCT Filed: Dec. 18, 2013

(86) PCT No.: PCT/US2013/076156
§ 371 (c)(1),
(2) Date: Jun. 4, 2015

(87) PCT Pub. No.: WO2014/100199
PCT Pub. Date: Jun. 26, 2014

(65) Prior Publication Data
US 2015/0316539 A1   Nov. 5, 2015

Related U.S. Application Data

(60) Provisional application No. 61/739,446, filed on Dec. 19, 2012.

(51) Int. Cl.
*G01N 33/50* (2006.01)
*C12N 5/079* (2010.01)

(52) U.S. Cl.
CPC ....... *G01N 33/5058* (2013.01); *C12N 5/0622* (2013.01); *G01N 2500/10* (2013.01)

(58) Field of Classification Search
CPC ............. C12N 5/0062; G01N 33/5058; G01N 2500/10
See application file for complete search history.

(56) References Cited

U.S. PATENT DOCUMENTS

| | | |
|---|---|---|
| 2009/0191626 A1 | 7/2009 | Shogbon et al. |
| 2009/0208975 A1 | 8/2009 | D'Costa et al. |
| 2011/0121431 A1 | 5/2011 | Cui et al. |
| 2011/0135814 A1 | 6/2011 | Miyauchi et al. |
| 2011/0207126 A1 | 8/2011 | Popko et al. |
| 2012/0172375 A1 | 7/2012 | Trapp et al. |

FOREIGN PATENT DOCUMENTS

| | | |
|---|---|---|
| WO | WO 2010/150521 A1 | 12/2010 |
| WO | 20120086028 | 6/2012 |

OTHER PUBLICATIONS

Chan et al. (2004) "NGF Controls Axonal Receptivity to Myelination by Schwann Cells or Oligodendrocytes" Neuron 43:183-191.
Colello and Pott (1997) "Signals that Initiate Myelination in the Developing Mammalian Nervous System" Mol. Neurobiol. 15:83-100.
Fan et al. (2012) "Directional Neurite Outgrowth on Superaligned Carbon Nanotube Yarn Patterned Substrate" Nano Letters 12(7):3668-3673.
Hakak et al. (2001) "Genome-wide expression analysis reveals dysregulation of myelination-related genes in chronic schizophrenia" PNAS 98(8):4746-4751.
Joubert et al. (2010) "Chemical inducers and transcriptional markers of oligodendrocyte differentiation" J Neurosci Res. 88(12):2546-2557.
Karadottir and Stockley (2012) "Deconstructing myelination: it all comes down to size" Nat Methods 9(9):883-884.
Kotter et al. (2011) "Enhancing remyelination in disease—can we wrap it up?" Brain, pp. 1-19.
Lee et al. (2009) "Highly oriented electrospun polycaprolactone micro/nanofibers prepared by a field-controllable electrode and rotating collector" Appl Phys A 97:559-565.
Lee et al. (2012) "A culture system to study oligodendrocyte myelination processes using engineered nanofibers" Nat Methods 9(9):917-922.
Lee et al. (2013) "A rapid and reproducible assay for modeling myelination by oligodendrocytes using engineered nanofibers" Nat Protoc. 8(4):771-782.
Voyvodic (1989) "Target size regulates calibre and myelination of sympathetic axons" Nature 342:430-433.
Zhang et al. (2011) "Central nervous system remyelination in culture—A tool for multiple sclerosis research" Exp Neurol. 230:138-148.
Zhang et al. (2011) "Quetiapine enhances oligodendrocyte regeneration and myelin repair after cuprizone-induced demyelination" Schizophr Res. 138(1)8-17.
Cao et al. (2013) "The possible influence varying diameter of aligned electrospun fibers on Schwann cells maturation in culture" Medical Hypotheses 81(5):887-888.
Mei et al. (2014) "Micropillar arrays as a high-throughput screening platform for therapeutics in multiple sclerosis" Nature Medicine 20(8):954-960.

*Primary Examiner* — Gregory S Emch
(74) *Attorney, Agent, or Firm* — Edward J. Baba; Shweta Chandra; Bozicevic, Field & Francis LLP

(57) ABSTRACT

Micropillar arrays for assaying differentiation of oligodendrocyte precursor cells into oligodendrocytes, ensheathment, and/or wrapping of the micropillars by the oligodendrocytes is provided. Also provided herein are methods of using the micropillar arrays for screening of candidate agents that promote differentiation of oligodendrocyte precursor cells into oligodendrocytes, ensheathment, and/or wrapping of the micropillars by the oligodendrocytes. A system comprising micropillar arrays and oligodendrocyte precursor cells are also provided.

14 Claims, 8 Drawing Sheets

FIGS. 3(a)-3(b)
a. Control  +quetiapine fumerate
 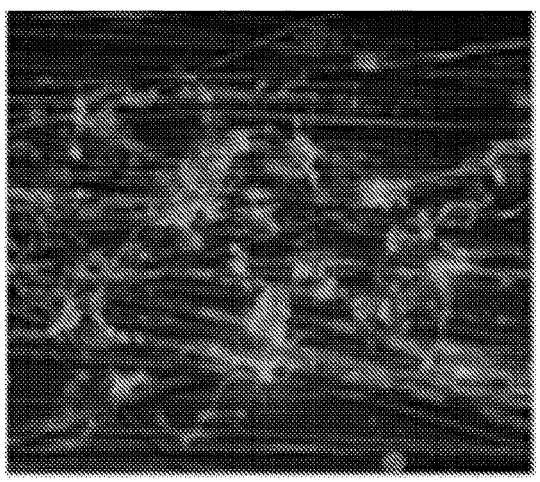
b. Control  +quetiapine fumerate
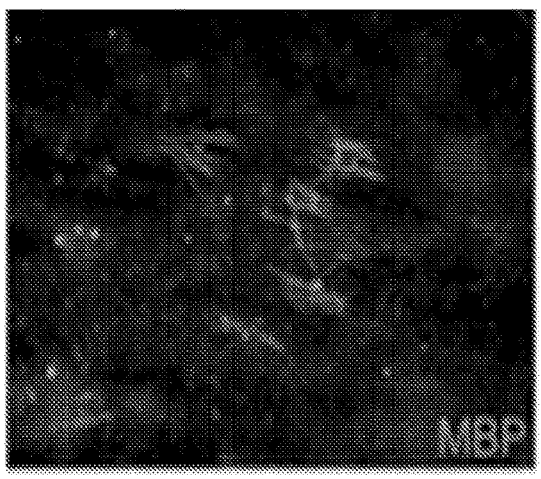 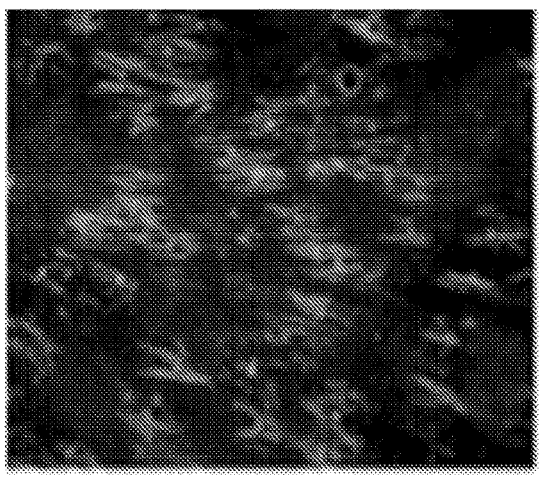

MICROPILLAR ARRAYS FOR ASSAYING MYELINATION

CROSS-REFERENCE

This application claims the benefit of U.S. Provisional Patent Application No. 61/739,446 filed Dec. 19, 2012, which application is incorporated herein by reference in its entirety.

STATEMENT REGARDING FEDERALLY SPONSORED RESEARCH

This invention was made with government support under Grant No. NS062796 awarded by the US National Institutes of Health/National Institute of Neurological Disorders. The government has certain rights in the invention.

INTRODUCTION

Myelin is a vital component of the central and peripheral nervous system. The systematic wrapping of an axon by insulating myelin sheaths is a remarkable event in the development of the vertebrate central nervous system. Consisting of 70% lipid and 30% protein, myelin is formed both by oligodendrocytes (OLs) in the central nervous system (CNS) and by Schwann cells in the peripheral nervous system (PNS). Working as insulation, myelin enhances the speed and integrity of nerve signal propagation down the neural axon, allowing signals to pass back and forth between the brain and the nerves of the periphery over long distances. Damage to the myelin sheath can lead to a variety of neurological disorders with often devastating consequences.

Damage to myelin in diseases such as multiple sclerosis (MS) results in the disruption of the nerve signal, damage to the axon, and finally neuronal degeneration. In order to effectively treat these devastating conditions, it is essential to develop novel methodologies and approaches to promote repair.

To date, there are no therapies for repair or remyelination in MS and this fact alone illustrates the greatest hope and unmet need for MS patients. Functional screening for small molecules or biologicals that promote remyelination represents a major hurdle to the identification and development of rational therapeutics for MS.

Therefore, it is imperative to continue to make technical advances in the development of high-throughput screening platforms that will provide insight into the cell autonomous mechanisms for remyelination.

SUMMARY OF THE INVENTION

Micropillar arrays for assaying myelination are provided. The micropillar arrays may be used for assaying differentiation of oligodendrocyte precursor cells into oligodendrocytes, and/or ensheathment, and/or wrapping of the micropillars by the oligodendrocytes is provided. Also provided herein are methods of using the micropillar arrays for screening of candidate agents that promote differentiation of oligodendrocyte precursor cells into oligodendrocytes and/or ensheathment and/or wrapping of the micropillars by the oligodendrocytes. A system comprising micropillar arrays and oligodendrocyte precursor cells are also provided.

BRIEF DESCRIPTION OF THE DRAWINGS

FIGS. 3(*a*)-3(*b*) illustrates the effect of quetiapine fumarate on myelination of nanofibers.

DETAILED DESCRIPTION

Figures 1A, 1B, 1C, 1D, 1E, 1F, 1G:
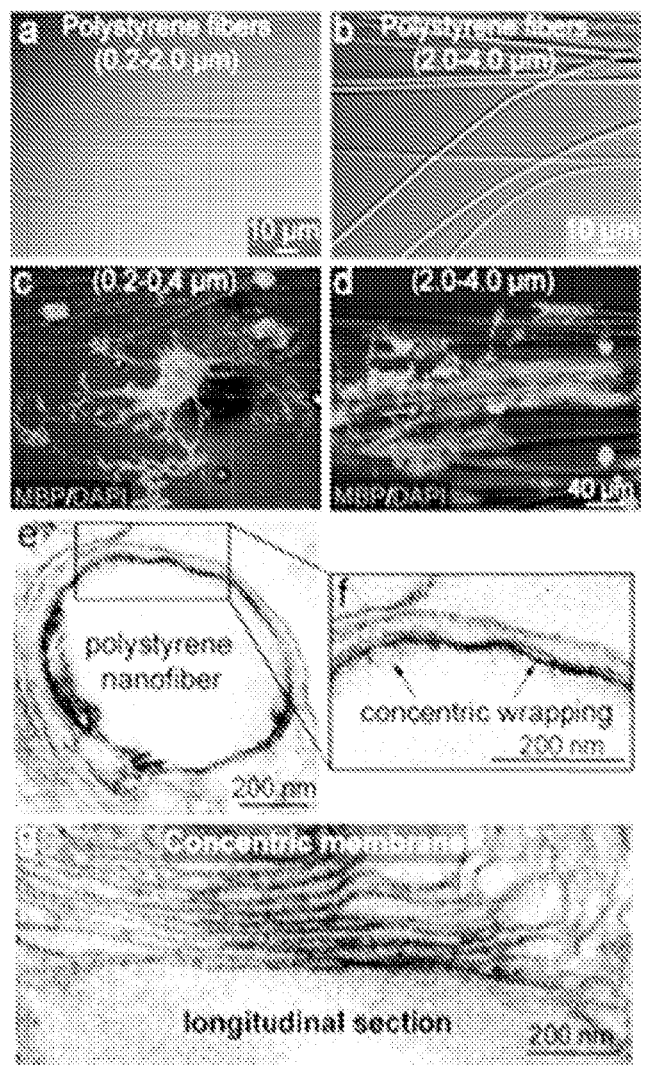
FIGS. 1(*a*)-1(*g*) illustrate use of nanofibers of different diameters to study myelination.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a micropillar" includes a plurality of such micropillars and reference to "the chamber" includes reference to one or more chambers and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Micropillar arrays for assaying level of myelination are provided. The micropillar arrays may be used to assay differentiation of oligodendrocyte precursor cells into oligodendrocytes and/or ensheathment and/or wrapping of the micropillars by the oligodendrocytes is provided. Also provided herein are methods of using the micropillar arrays for screening of candidate agents that promote differentiation of oligodendrocyte precursor cells into oligodendrocytes and/or ensheathment and/or wrapping of the micropillars by the oligodendrocytes. A system comprising micropillar arrays and oligodendrocyte precursor cells are also provided.

Micropillar Arrays for Assaying Myelination

As noted above, micropillar arrays that are suitable for use in a method for screening for candidate agents that promote myelination is provided.

The micropillar arrays include a substrate that includes a plurality of micropillars. The plurality of micropillars includes micropillars that project vertically from the substrate. In certain embodiments, the micropillars may have a shape that tapers in diameter from a base of the micropillars attached to the substrate to a tip of the micropillars projecting away from the substrate.

In general, the micropillars of a micropillar array have a uniform size. In certain embodiments, the micropillars have a base ranging in diameter from 10 µm to 150 µm and a tip ranging in diameter from 0.1 µm to 8 µm. In certain cases, the base ranges in diameter from 25 µm to 50 µm and the tip ranges in diameter from 1 µm to 5 µm. In certain cases, the base ranges in diameter from 25 µm to 40 µm, such as, about 25 µm, 30 µm, 35 µm, or 40 µm. In certain cases, the tip ranges in diameter from 2 µm to 4 µm. In certain cases, the diameter of the tip is about 1 µm, 2 µm, 3 µm, 4 µm, or 5 µm.

In certain embodiments, the micropillars have a height between the tip and the base ranging from 15 µm to 50 µm. In certain cases, the height between the tip and the base ranges from 25 µm to 50 µm. In certain cases, the height between the tip and the base is 25 µm, 30 µm, 35 µm, or 40 µm.

In general, the plurality of micropillars of a micropillar array has a uniform shape. The shape of the micropillars, as viewed from the side (i.e., along the z-axis if the plane is defined by x- and y-axis), may be conical, frusto-conical, bi-conical, or parabolic.

In certain embodiments, the plurality of micropillars on the substrate may be separated from each other by a uniform distance. Accordingly, in certain cases, the micropillars may be positioned at a distance of about 1 mm from each other, such as, 800 µm, 600 µm, 400 µm, 200 µm, 150 µm, 100 µm, 50 µm, or 25 µm of intervening space between the micropillars. The distance in between the micropillars may be the distance between the base of the micropillars. The distance in between the micropillars may be the distance between the periphery of base of the micropillars.

In certain embodiments, the micropillar array is addressable. An "addressable array" includes any one or two dimensional arrangement of a plurality of micropillars positioned at a particular location on the substrate (an "address").

In certain embodiments, the substrate may include a plurality of chambers and the plurality of chambers may each include a plurality of micropillars. In such embodiments, the micropillar array is addressable as the location of each of the chambers on the substrate is known.

In certain cases, the substrate may be a substantially planar substrate from which the plurality of micropillars vertically project. In certain cases, the planar substrate may have a two-dimensional shape, including, a square, or a rectangle. However, the planar substrate may be in other shapes, such as, circular, triangular, or the like. The term "substantially" as used herein refers to at least 70%, 80%, 90%, 99%, or 100%. For example, the phrase "substantially planar substrate" refers to a substrate that is at least 70%, 80%, 90%, 99%, or 100% planar.

In certain embodiments, the substrate may include a plurality of chambers, wherein the plurality of chambers may range from 2-1536 chambers. In certain cases, the substrate may include about 6, 24, 96, 384 or 1536 chambers. The volume of the chamber may range from about 1 ml-50 µl, such as, about 500 µl-50 µl, such as, about 400 µl, about 350 µl, about 300 µl, about 200 µl, about 100 µl, or about 50 µl. The term "about" as used herein refers to a difference of no more than 0.1%, no more than 0.5%, no more than 1%, no more than 2% or more, no more than 5%, or no more than 10% from the specified value. In certain cases, the plurality of chambers may be wells or microwells.

In certain embodiments, the dimension of the substrate comprising the micropillars may be that of standard cell culture dishes. Use of such substrates may facilitate determining of presence or absence of myelination on the micropillars, using a microscope for example.

In general, the chambers may be open on the top to provide for addition of reagents, cells, candidate agents, and the like, to the chamber. The chambers may be covered by a removable lid.

In certain embodiments, the plurality of chambers may each contain the plurality of micropillars, where the number of micropillars present in the chambers may range from 10-200, such as, 20-200, 30-150, 40-120, 50-100, for example, 20, 30, 40, 50, 60, 80, 100, 120, 140, 180, or 200.

In general, the micropillars are made from a material that is conducive to culture of cells, such as, oligodendrocyte precursor cells (OPCs) or oligodendrocytes. Any material that is compatible with supporting culturing of cells may be used to manufacture the micropillars. In general, cell culture substrates such as, polystyrene, polypropylene, or silica may be used. In certain cases, the micropillars may be made form a material selected from the group consisting of polypropylene, polystyrene, polyvinyl chloride, acrylonitrile butadiene styrene, styrene butadiene copolymers, polyethylene terephthalate, and silica.

The micropillar arrays may be fabricated by any convenient method. Exemplary methods include etching a substrate surface to produce the micropillars, deposition of a polymer on a substrate to fabricate the micropillars, injection molding, or the like. A substrate that includes a plurality of chambers which include the micropillars may be fabricated by a variety of methods. For example, a prefabricated substrate with a plurality of chambers, such as, a multi-well cell culture plate may be used to introduce micropillars into the chambers. In another exemplary method, a substrate that includes a plurality of micropillars that are positioned uniformly on the substrate may be bonded to a grid providing a plurality of chambers.

The substrate that includes the micropillars may be transparent or semi-transparent permitting visualization of the micropillars and cells present on the substrate. In this context, the term "transparent" refers to permitting any interrogating radiation to pass therethrough without substantial attenuation and also permitting the signal from features to pass therethrough without substantial attenuation or distortion. By "without substantial attenuation" may include, for example, without a loss of more than 40%, more than 30%, more than 20% or more than 10%. The interrogating radiation and signal may for example be visible, ultraviolet or infrared light.

Screening Methods

A method for screening for candidate agents that promote myelination is also disclosed herein. In certain embodiments, the method may include incubating a candidate agent with a substrate comprising a plurality of micropillars and oligodendrocyte precursor cells (OPCs); determining presence or absence of myelination on the plurality of micropillars, where the presence of myelination on the plurality of micropillars indicates that the candidate agent promotes myelination.

In certain embodiments, the substrate comprising a plurality of micropillars is as described in the foregoing section.

In certain embodiments, the substrate may include a plurality of chambers and the plurality of chambers may each include a plurality of micropillars and the OPCs.

In certain embodiments, the method may include incubating a plurality of candidate agents with the substrate comprising the plurality of chambers and the OPCs, wherein the plurality of chambers each comprise a different candidate agent.

A myriad of methods may be used for determining presence or absence of myelination on the micropillars.

In certain embodiments, the determining presence or absence of myelination may involve assaying for differentiation of OPCs into myelin producing glia cells, such as, oligodendrocytes, wherein the assaying may include detecting of ensheathment of the plurality of micropillars by the oligodendrocytes.

In certain embodiments, the determining presence or absence of myelination may involve assaying for concentric wrapping on the plurality of micropillars by oligodendrocytes generated from the OPCs.

In certain embodiments, the determining presence or absence of myelination may include determining a level of myelination.

As used herein, myelination refers to the ensheathment of a micropillar by an oligodendrocyte. The ensheathment may include a layer of myelin sheath wrapping around the micropillar at least once. The ensheathment may encompass complete or partial wrapping around a region of the micropillar where the region is at the tip or base of the micropillar or in between the tip and the base of the micropillar. Partial wrapping may include wrapping of at least 60%, or 70%, or 80%, or 90% of the circumference of the micropillar at the tip or the base of the micropillar or at a region in between the tip and the base of the micropillar. Complete wrapping refers to wrapping around the circumference of the micropillar, where the wrapping is at least about 95%, or 99%, or 100% of the circumference of the micropillar at the tip or the base of the micropillar or at a region in between the tip and the base of the micropillar. Accordingly, complete wrapping refers to presence of a myelin ring around a circumference of the micropillar.

Concentric wrapping of the myelin sheath around the micropillar refers to wrapping of a circumference of the micropillar at the base, or the tip, or a region in between the tip and the base, multiple times, such as, 2, 3, 4, 5, or more times. Accordingly, concentric wrapping of the myelin sheath around the micropillar refers presence of two or more myelin rings around a circumference of the micropillar.

The phrase, level of myelination, as used herein refers to the amount of myelin sheath present on the micropillars. In certain embodiments, a level of myelination above a background threshold but below a concentric wrapping threshold may indicate that the micropillars are ensheathed but concentric wrapping has not occurred. In certain embodiments, a level of myelination above a background threshold and at or above a concentric wrapping threshold may indicate that the micropillars are ensheathed and concentric wrapping has occurred. The level of myelination above the concentric wrapping threshold may indicate the degree of concentric wrapping on the micropillar.

The thresholds may be set based on negative and positive controls. For example, the thresholds may be set based on the method for assaying myelination, number of OPCs, and/or number of micropillars. A background threshold may be selected based on the signal obtained from a micropillar array that includes cells that do not differentiate into oligodendrocytes; signal obtained from a micropillar array containing oligodendrocytes that have been contacted with a non-specific antibody. A negative control may also provide a background threshold—for example, in the context of a screen, the negative control may be micropillars and OPCs that are not contacted by a candidate agent.

Concentric wrapping threshold may be determined from a positive control. In certain embodiments, a molecule known to promote myelination may be used determine concentric wrapping threshold. Molecules, such as, thyroid hormone or quetiapine fumarate can be used to determine concentric wrapping threshold.

In certain embodiments, the determining presence or absence and/or level of myelination may be performed by using a processor and a memory comprising instructions, when executed by the processor, cause the processor to determine the presence or absence and/or level of myelination on the plurality of micropillars. In certain embodiments, the determining presence or absence and/or level of myelination may be automated.

In certain embodiments, the determining the presence or absence and/or level of myelination on the micropillars may be carried out by detecting an oligodendrocyte (OL) specific marker.

Any known OL specific marker may be used. In certain cases, the marker may be myelin basic protein (MBP), proteolipid protein (PLP or lipophilin), or a marker encoded by a reporter gene whose expression is driven by an OL specific promoter that drives expression in oligodendrocytes (OLs), for example. Exemplary promoters that may be utilized to provide expression of an OL specific marker include promoters for MBP, PLP, and the like. In certain embodiments, the OLs used in the methods and systems disclosed herein may be genetically modified OLs that encode a fluorescent protein or a bioluminescent protein from a gene operably-linked to an OL specific promoter. "Operably-linked" refers to the association of nucleic acid sequences on a single nucleic acid fragment so that the function of one is affected by the other. For example, a promoter is operably-linked with a coding sequence or functional RNA when it is capable of affecting the expression of that coding sequence or functional RNA (i.e., the coding sequence or functional RNA is under the transcriptional control of the promoter). An expression cassette that includes the MBP promoter and drives the expression of a gene operably-linked to the promoter and provides a marker for OLs is described in WO2011084281A1, which is herein incorporated by reference in its entirety.

In certain cases, the screening of the candidate agents may be performed in a high-throughput manner utilizing a micropillar array comprising a substrate comprising a plurality of chambers comprising a plurality of micropillars. Candidate agents of interest may be incubated with OPCs added to the different chambers. The addition of OPCs and the candidate agents may be performed robotically in certain cases. The micropillar arrays may be monitored using a microscope and the signal obtained from the chambers may be analyzed using a processor and a memory comprising instructions, when executed by the processor, cause the processor to determine the presence or absence and/or level of myelination on the plurality of micropillars. The instructions may include background threshold level, concentric wrapping threshold level, and the like.

In certain cases, the detecting determining the presence or absence and/or level of myelination on the micropillars may be carried out may be carried out at different time points during the incubating of the candidate agents with the substrate comprising a plurality of micropillars and OPCs. As such, the initial determining may reveal whether a candidate agent promotes conversion of the OPCs into OLs. A determining performed at a later stage may reveal whether the OLs were capable of ensheathing the micropillars. A determining performed at a further later time point may reveal whether the OLs were capable of concentrically wrapping the micropillars.

The incubating of one or more candidate agents with the substrate comprising a plurality of micropillars and OPCs may be carried out for a period of time ranging from 1 day to 30 days. In certain cases, the incubating may be done for, such as, at least about 1 day, 2 days, 4 days, 6 days, one week, 10 days, two weeks, 18 days, three weeks, 25 days, four weeks, or more. The determining of presence or absence of myelination may be performed at any number of day(s) after the incubating step is started. In certain cases, the presence or absence of myelination and/or level of myelination may be monitored using a time-lapse microscope, such as, a fluorescent time-lapse microscope.

The incubating may be carried out under conditions suitable for culture of OPCs, OLs, glial cells, Schwann cells, and the like. Suitable cell culture conditions are known to a person of ordinary skill in the art. Suitable cell culture conditions may be optimized based on the type of OPCs, OLs, and the like. Various media are commercially available and may be used according to the nature of the cells, including Dulbecco's Modified Eagle Medium (DMEM), Hank's Balanced Salt Solution (HBSS), Dulbecco's phosphate buffered saline (DPBS), RPMI, Iscove's medium, which may be supplemented with growth factors and other supplements that support viability of the cells.

A variety of OPCs may be used in the methods and systems disclosed herein. As used herein an oligodendrocyte precursor cell (OPC) may be a cell that is committed to differentiate and give rise to myelin producing glial cells, such as, oligodendrocytes (OLs or oligodendroglia or oligodendroglial cell). For example, the OPCs may be obtained from a subject of any specifies, such as, murine, equine, porcine, bovine, canine, feline, ovine or other species. In certain cases, the OPCs may be obtained from a human. In certain cases, the OPCs may be generated from pluripotent cells, such as, induced pluripotent cells, embryonic pluripotent cells, such as embryonic stem cells, mesenchymal stem cells (MSCs). In certain cases, the OPCs may be generated from multipotent cells. In certain cases, the OPCs may differentiate into OLs and/or Schwann cells.

In certain embodiments, the micropillar array may be read from the bottom using an inverted microscope. In certain cases, the micropillar array may be read from the top. The bottom of the micropillar array is the side of the substrate on which micropillars are not present. Accordingly, the top side of the micropillar array is the side of the substrate on which micropillars are present.

In certain embodiments, the method may involve a screening for a candidate agent by using a binary indicant of myelination, i.e., whether or not myelination is present based on presence or absence of a marker specific for an oligodendrocyte.

In certain embodiments, the method may involve incubating a candidate agent with a substrate comprising a plurality of micropillars and oligodendrocyte precursor cells (OPCs), where the number of OPCs ranges from 20,000-100,000. The number of OPCs to be used in the method can be ascertained based on the type of assay, the number of micropillars, size of substrate, size of chambers, and the like.

In certain cases, the method may involve incubating a candidate agent with a micropillar array comprising a substrate comprising a plurality of chambers, each of the chambers comprising a plurality of micropillars and a plurality of OPCs. The micropillar array may also comprise a plurality of chambers that lack micropillars and/or OPCs, which chambers may serve as a control for the determining of presence or absence of myelination and/or level of myelination. In certain embodiments, the number of OPCs included in a chamber may be based on the size of the chamber and/or the number of micropillars in the chamber. In certain cases, each of the chambers may include about 100,000; 80,000; 60,000; 40,000; 20,000; 10,000; 5,000; 3000; 1000; 300; 200; 100; 80; 60; 50; 30; 20; 10; or lesser OPCs.

In certain cases, candidate agents of interest for screening include biologically active agents of numerous chemical classes, primarily organic molecules, although including in some instances inorganic molecules, organometallic molecules, immunoglobulins, etc. Also of interest are small organic molecules, which comprise functional groups necessary for structural interaction with proteins, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof.

Compounds may be obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

A plurality of assays may be run in parallel with different concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable presence of myelination.

In general, the methods and systems described herein do not require neurons. As such, the method and the systems provided herein do not include a substantial number of neurons. In certain embodiments, the OPCs may have a small number of contaminating neurons. In general, the percent of neurons that may be present in the OPCs population present in the methods and systems disclosed herein may be less than 30%, less than 20%, less than 10%, less than 5%, less than 1%, or less than 0.5%. In certain embodiments the percent of neurons that may be present in the OPCs population present in the methods and systems disclosed herein may be 0%.

A candidate agent identified as promoting myelination may be further characterized by analyzing the density of myelin sheath wrapped around the micropillar upon incubating the agent with the micropillar array and OPCs. The candidate agent(s) may be validated further using standard in vitro assays for myelination. Candidate agents validated in vitro may be further tested in animal models for diseases associated with loss of myelination (demyelination). Candidate agents validated as promoter of myelination in vivo may then be tested in subjects with conditions associated with loss or lack of axon myelination. In some embodiments, the axons are CNS axons. Such conditions may include trauma, toxin exposure, asphyxia or hypoxia-ischemia, perinatal hypoxic-ischemic injury, injury to or disease of the white matter of the central nervous system, acute brain injury, Creutzfeld-Jakob disease, chronic neurodegenerative disease, and demyelinating diseases. Multiple sclerosis is of particular interest. The demyelinating diseases and disorders may include acute disseminated encephalomyelitis, optic neuritis, transverse myelitis, Devic's disease, the leucodystrophies, progressive multifocal leukoencephalopathy, and central pontine myelinolysis.

Chronic demyelinating conditions may include chronic immune demyelinating polyneuropathy (CIDP); multifocal CIDP; multifocal motor neuropathy (MMN), anti-MAG syndrome; galop syndrome; anti-sulfatide antibody syndrome (with serum M-protein); anti-GM2 antibody syndrome; POEMS syndrome; perineuritis; and the like.

Systems for Assaying Myelination

Also provided herein are systems for assaying myelination. These systems can be used to assess whether a molecule of interest affects myelination. In certain embodiments, this system may be used identify candidate agents that increase or decrease myelination.

The system may include a substrate comprising a plurality of micropillars; and oligodendrocyte precursor cells (OPCs), wherein the plurality of micropillars comprise micropillars that project vertically from the substrate and comprise a shape that tapers in diameter from a base of the micropillars attached to the substrate to a tip of the micropillars projecting away from the substrate.

The substrate comprising the plurality of micropillars is provided in the preceding sections.

Accordingly, in certain embodiments, the substrate may include a plurality of chambers and wherein the plurality of chambers comprises the plurality of micropillars and the OPCs.

The OPCs that may be included in the systems are described in the preceding section.

In certain cases, the system may further include a processor; and a memory comprising instructions, when executed by the processor, cause the processor to determine the presence or absence and/or level of myelination on the plurality of micropillars.

The instructions may include information regarding threshold(s) for determining presence or absence of myelination; threshold(s) for determining level of myelination; and the like.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1

Nanofibres Support Myelination

It has long been thought that myelination is a result of axonal signaling to oligodendrocytes (Colello and Pott, Mol. Neurobiol. 15, 83-100, 1997). Therefore, identifying the nature of these signals is paramount to promoting repair and is indeed the goal of most myelination research. It is generally accepted that induction of myelination is somehow intimately related to axonal diameter; larger axons are myelinated while smaller ones are not. An increase in axonal target size correlates with both an increase in axonal diameter and the development of myelin (Voyvodic, Nature 342, 430-433, 1989). However, this finding alone does not establish that an increase in axon diameter is sufficient to initiate myelination, but instead demonstrates that axonal signals encourage myelin development and are regulated by extrinsic factors. Our recent findings offer an intriguing and alternative hypothesis to challenge the role of axon diameter on the initiation of oligodendrocyte myelination. We engineered electron-spun polystyrene nanofibers to replace axons as a substrate allowing for the investigation of whether nanofibers could potentially act as a suitable scaffold for oligodendrocyte myelination (FIG. 1).

FIG. 1 (a) Polystyrene nanofibers ranging from 0.2-0.4 µm and (b) 2-4 µm in diameter were generated and imaged. Purified oligodendroglia were plated onto the fibers and observed to ensheath and wrap large fibers. The cultures were immunostained for myelin (red) and merged with phase contrast images of the fibers. (e-g) Compact wraps of membrane were observed by electron microscopy, indicative of myelination.

Our findings demonstrate that fiber diameter is indeed sufficient to initiate wrapping by oligodendrocytes and that myelination in the absence of axons represents a minimally permissive environment, one that is ideally suited for analyzing cell autonomous mechanisms necessary and sufficient for myelination (Lee et al., Nature Methods, 9 (9): 917-922, 2012). This recent finding allowed us to initiate small-scale screening efforts. The exquisite flexibility in the design of our nanofibers guarantees constant uniformity and density of fibers in the experimental design and any effects from compounds tested could be attributed solely to direct influences on oligodendroglia (FIG. 2), without confounding effects from neurons.

Figure 2:
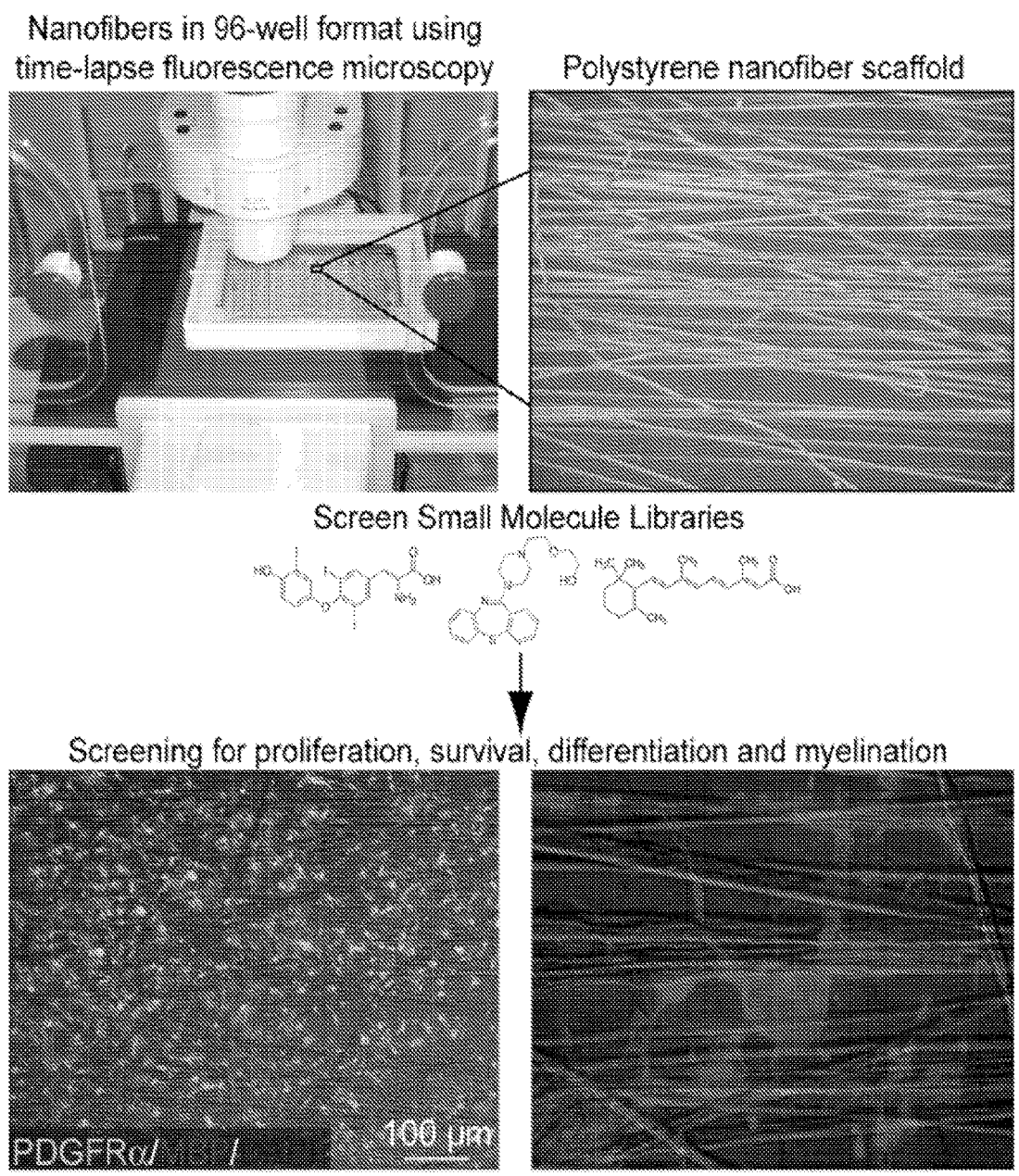
FIG. 2 depicts the use of nanofibers to study myelination in the presence of candidate small molecules.

FIG. 2. Nanofibers are patterned and deposited into a 24-well format and placed under an automated fluorescence microscope with incubation chamber. Upon addition of oligodendroglia and small molecules, cells cultured with the nanofibers can be analyzed for effects on proliferation, survival, differentiation, and myelination in real time. Myelination in the absence of axons represents a minimally permissive environment, one that is ideally suited for analyzing cell autonomous mechanisms necessary and sufficient for the processes preceding and leading to myelination. The bottom panels illustrate the proof of principle that oligodendrocyte precursor cells (green) and oligodendrocytes (red) can be cultured on the nanofibers and that myelination can be identified (red).

To initiate a screen, a candidate list of known molecules and chemical inhibitors thought to play a role in promoting oligodendrocyte differentiation and myelination was compiled, and applied various FDA approved compounds in the treatment of psychiatric disorders. As multiple studies have correlated abnormalities in myelin ultrastructure and extent in mental disorders like schizophrenia, atypical antipsychotics and dopamine receptor antagonists were screened (Hakak et al., PNAS, 98 (8): 4746-4751, 2001; McDonald et al., 2005). We found that the compound quetiapine fumarate (Seroquel) greatly enhanced differentiation of oligodendrocytes and myelination of the nanofibers (FIG. 3a). In order to validate these findings we analyzed the effects of quetiapine on purified oligodendroglia cocultured with purified neurons. Quetiapine fumarate significantly enhances differentiation and myelination of neuronal axons (FIG. 3b). In the cocultures, myelin internodes can be routinely identified by the "tube-like" structures (immunostained for myelin-specific proteins) formed by the oligodendrocytes. The concentric and compact membrane wraps can also be detected by electron microscopy (Chan et al., Neuron 43, 183-191, 2004). Overall, the coculture system recapitulates the timing of oligodendrocyte development and myelination in vivo and represents a powerful tool to validate compounds and factors that may both promote and inhibit oligodendroglial development. Interestingly, as quetiapine was originally developed as a dopamine-2 (D2) receptor antagonist, other D2 antagonists did not elicit the same effects on the oligodendrocytes. The significance of this finding is the identification of a candidate molecule with the potential to promote repair in multiple sclerosis. Additionally, the ability to quantify a functional readout for differentiation and myelination by oligodendrocytes, provides the unique opportunity to uncouple the axonal contribution on myelination.

FIG. 3. Oligodendrocyte differentiation and myelination were examined on our nanofiber platform (a). Quetiapine fumarate greatly enhanced differentiation and myelination of our fibers. (b) Oligodendrocyte-DRG neuronal cocultures were established to validate the effects of quetiapine fumarate (100 nM). Cultures were immunostained after 7 days in vitro and analyzed for myelin basic protein (red). As indicated by the figure, oligodendrocyte differentiation and myelination were significantly accelerated.

This finding provides the rationale for this approach and will impart valuable insight into the identification of additional compounds and biologicals that may promote development, stability and repair. However, high throughput analysis of small molecules and compounds remains unattainable, as the nanofibers cannot be patterned into microwells without great difficulty. Additionally, automated imaging systems cannot identify "myelin segments" in a rapid and reproducible manner, making high throughput analysis impossible. To overcome these limitations, we sought to develop a binary system in a microwell platform to identify oligodendrocyte myelination allowing for the high throughput analysis of small molecules and compounds.

Example 2

Micropillar Arrays for Assaying Myelination

Developing a functional screen necessitates the ability to conduct experiments rapidly, in a robust, reproducible and quantitative manner. While we have clearly demonstrated that the nanofiber scaffold represents an advance in screening compounds, the fibers are not suitable for high-throughput screening. Spinning and patterning the nanofibers into small wells can only be accomplished with great difficulty and is extremely time-consuming. Additionally, automated software to identify and quantify myelin internodes is not currently available.

Figures 4A, 4B, 4C:
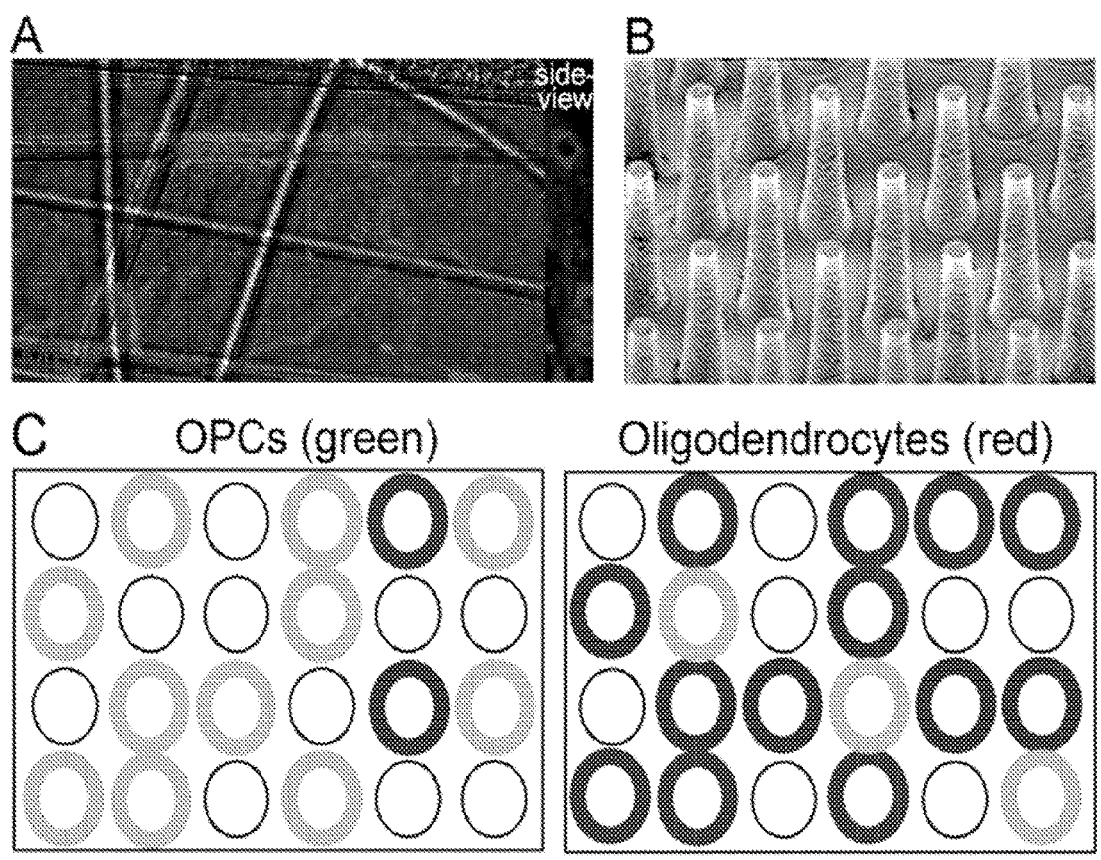
FIGS. 4A-4C provide a schematic of a binary indicant for myelination using micropillar arrays.

Micropillar arrays were fabricated from compressed silica (fabricated by Trianja Technologies). The arrays were designed on chips suitable for a 96-well format permitting for a more efficient and rapid experimental design. The micropillars allow for visualization of myelination in cross-section, a feature that will allow for the detection of "rings" of myelin (FIG. 4). As micropillars can be fabricated into any size and orientation, we have designed a template for micropillars that are approximately 50 µm in height (Lee et al., supra) and 2 µm in diameter (permissive for myelination; Lee et al., supra) at the top of the pillar with a base of 150 µm. This format will allow for an analysis of the optimal pillar specification. Micropillars are spaced at 120 µm intervals to allow for a reasonable number of oligodendroglia to adhere between the pillars. Using Axiovision software by Zeiss, we can automate the detection and quantification of the number of myelin rings without any of the confounding issues associated with the nanofibers (i.e. length of internodes, interfering cell processes, cell bodies, etc.). Essentially, oligodendrocyte precursor cells (OPCs) will be visualized as green rings whereas oligodendrocytes are indicated as red rings (FIG. 4C).

FIG. 4. A binary indicant for myelination using micropillar arrays. (a) Oligodendrocyte wrapping of a nanofiber can be visualized from the side as a "ring" of myelin (red, MBP positive staining) (b) Micropillars can be fabricated into any size and orientation. We have fabricated a template for micropillars that are approximately 50 µm in height with a diameter of 2 µm. Micropillars are spaced at 100 µm intervals to allow for cells to adhere to the surface. (c) Using an inverted fluorescence microscope, the pillars will be imaged from the bottom and identification of "rings" of myelin will be used as a binary indicant for functional myelination.

Figures 5A, 5B, 5C, 5D, 5E, 5F:
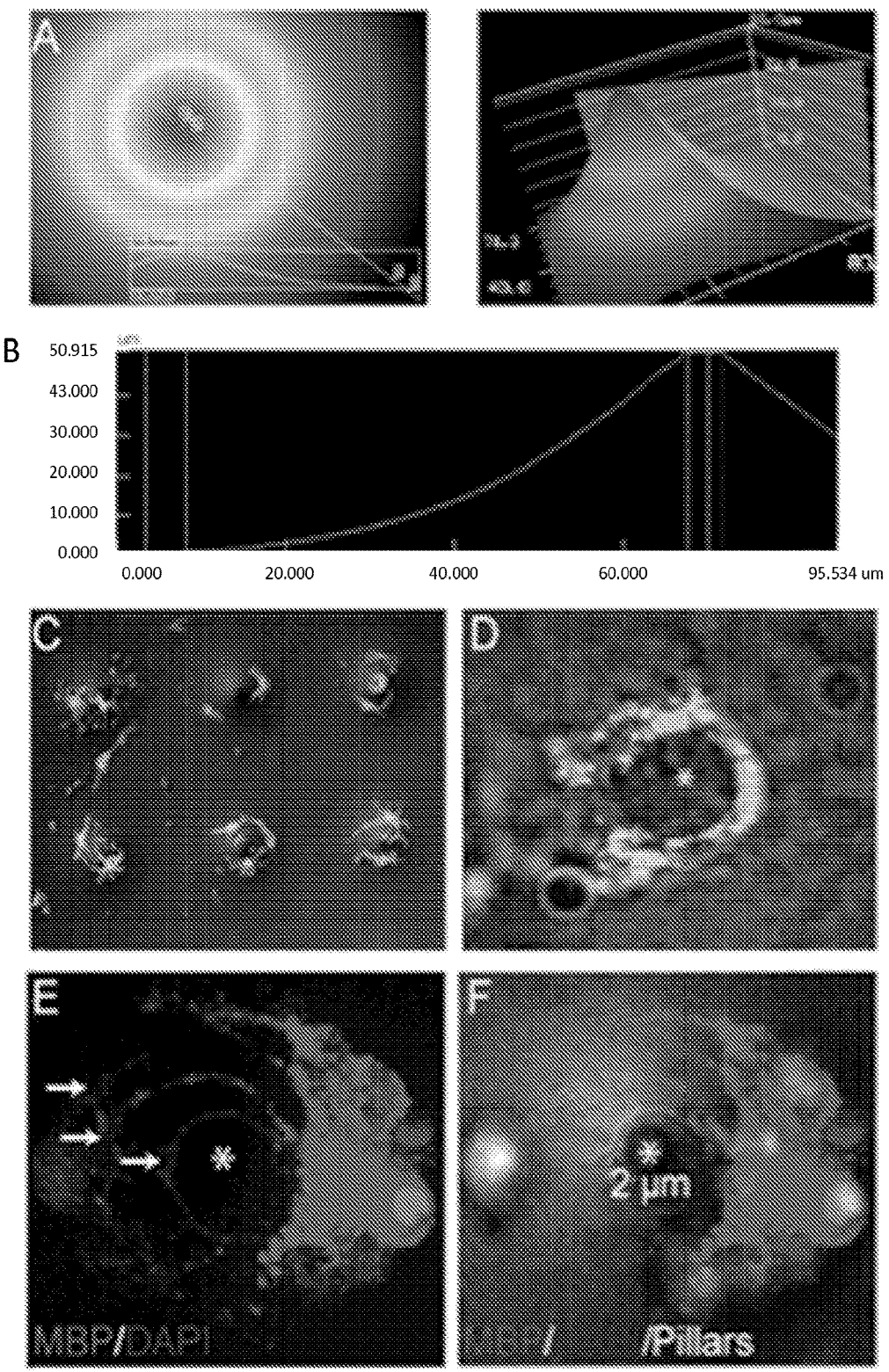
FIGS. 5A-5F depict the fabrication of micropillars and myelination.

To demonstrate the proof of principle in this approach, we fabricated the micropillars, analyzed the dimensions, and cultured primary OPCs in the arrays (FIG. 5). The OPCs ensheathed the micropillars along the entire length (FIG. 5C, D). Additionally, upon differentiation into oligodendrocytes, MBP positive cells concentrically wrap the pillars (FIG. 5E, F). Quantification of the wrapping illustrates that oligodendrocytes could not wrap the base of the pillars (150 µm) but preferred the smaller diameter top portion of the pillars. These results suggest that diminishing the diameter of the pillars would optimize the wrapping of oligodendroglial cells.

FIG. 5. Fabrication of micropillar arrays for myelination. (A, B) Micropillar arrays were fabricated from compressed silica and etched to dimensions that allowed for ensheathment and wrapping. Quantification of the size and distribution of the micropillars. (C, D) OPCs (green) were cultured with the micropillars and ensheathed the pillars along their entire length. (E, F) Oligodendrocytes (red) wrapped the pillars in a spiraled manner, indicative of myelination.

To analyze the possibility and effectiveness of using the micropillars as a screening platform, we plated the OPCs on the arrays and added molecules that have previously been shown to promote differentiation and wrapping, namely the quetiapine fumarate and thyroid hormone (FIG. 3, 6). As a proof of principle, quetiapine fumarate and thyroid hormone significantly enhanced the generation of "myelin rings" on the micropillar platform. Quantification of differentiation and myelination of the oligodendrocytes validated our previous findings on the nanofibers and cocultures and suggest that the micropillar arrays represent an effective screening platform for identifying compounds that promote differentiation and wrapping.

Figures 6A, 6B, 6C:
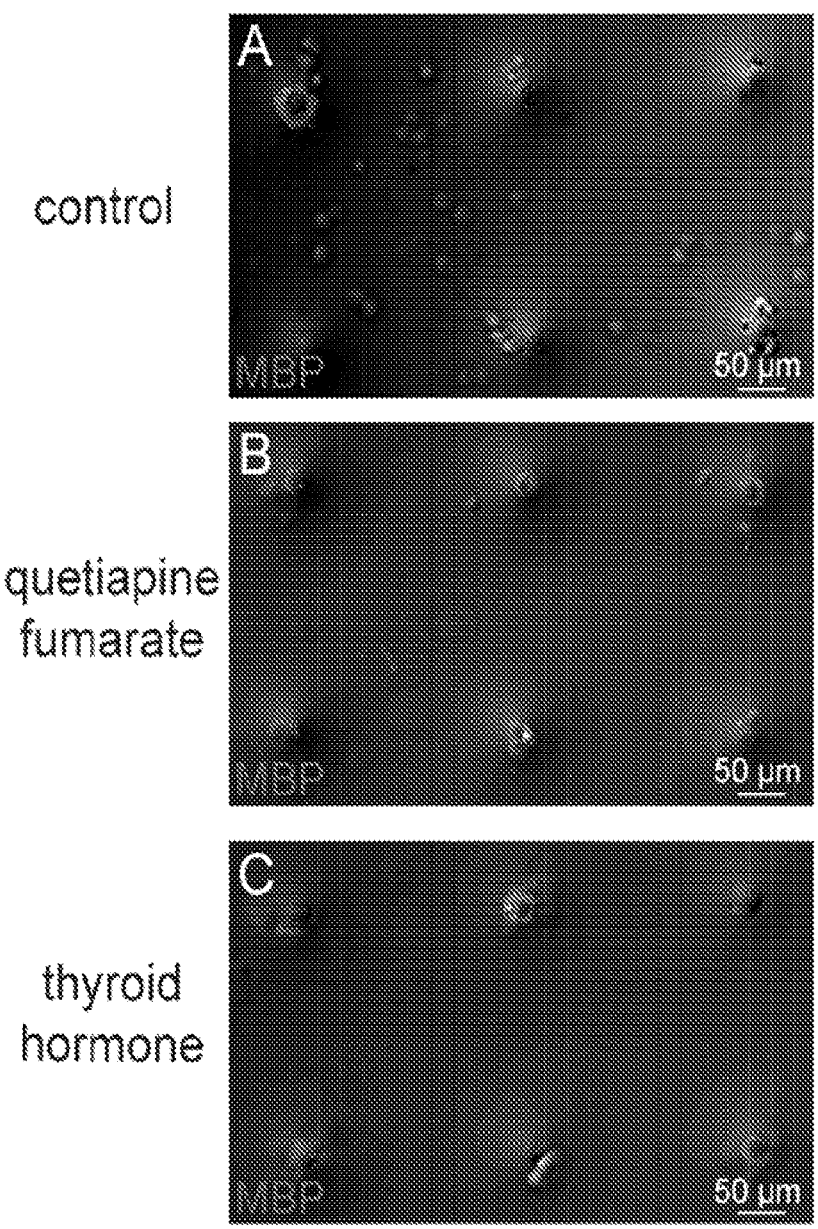
FIGS. 6A-6C illustrate that the use of micropillars to assay myelination.

FIG. 6. Proof of principle experiment illustrating that binary indicant of myelination assay (BIMA) identifies enhancement in oligodendrocyte myelination. (A-C) Immunostaining for myelination by oligodendrocytes (red, MBP positive staining) surrounding micropillars. Oligodendrocytes were cultured on micropillars for total of 6 days in vitro (div) and received compounds known to enhance differentiation at 4 div for two days. Compared to the (A) control, addition of either (B) 1 µM quetiapine fumarate or (C) 30 ng/mL thyroid hormone increases the number of red "myelin rings" generated by oligodendrocytes. Images were acquired at 6 div. Scale bar, 50 µm.

Example 3

Optimization of Micropillar Arrays

Upon further analysis of the data, we determined that the specification of the micropillar arrays needed to be altered. The first was the design in the aspect ratio of the pillars. As oligodendrocytes could not wrap the large base diameter of the pillars we decided to design the base of the pillars with a diameter of 50 µm. Maintaining a top pillar diameter of 2 µm, we decreased the height of the pillars to 25 µm to ensure the efficient ensheathment and wrapping. In order to ensure the identification of concentric wrapping of myelin membrane by oligodendrocytes we kept the gradual tapering of the pillars, as observed in FIG. 5E. The spacing of the micropillars (120 µm) was optimized to 50 µm to ensure that the number of oligodendroglial cells was matched to the density of micropillars. Finally, we patterned the array to be bonded into 96-microwell plates (FIG. 7).

Figure 7:
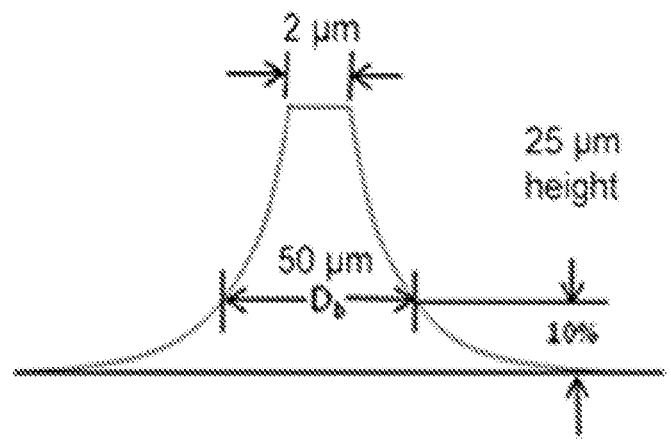
FIG. 7 illustrates a micropillar and a micropillar array in a 96 well plate according to an embodiment of the invention.
Figure 7:
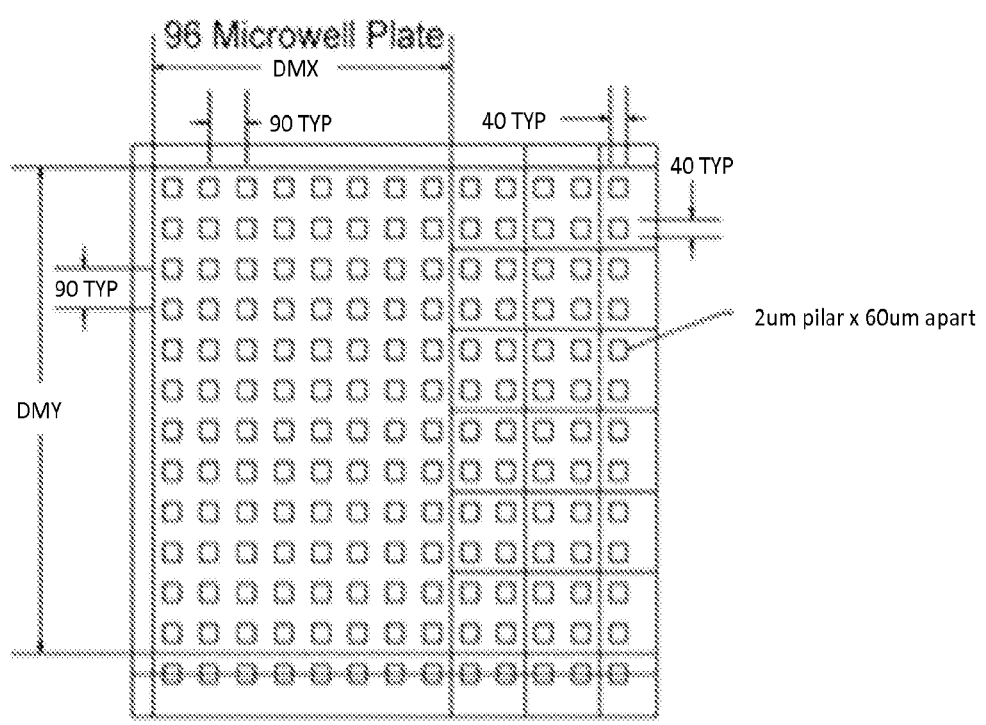

FIG. 7. Optimization of BIMA design to obtain efficient ensheathment and wrapping by oligodendroglial cells. The aspect ratio of the pillars was modified with a base diameter of 50 µm and a top diameter of 2 µm. The height of the pillars was decreased to 25 µm. The micropillars were fabricated to be bonded into 96 microwell plates. Each of the pillars will be spaced at 50 µm to ensure that the optimal density of cells to pillars will be achieved.

Example 4

Use of Micropillar Arrays to Study Kinetics of Myelination

Figures 8A, 8B, 8C, 8D:
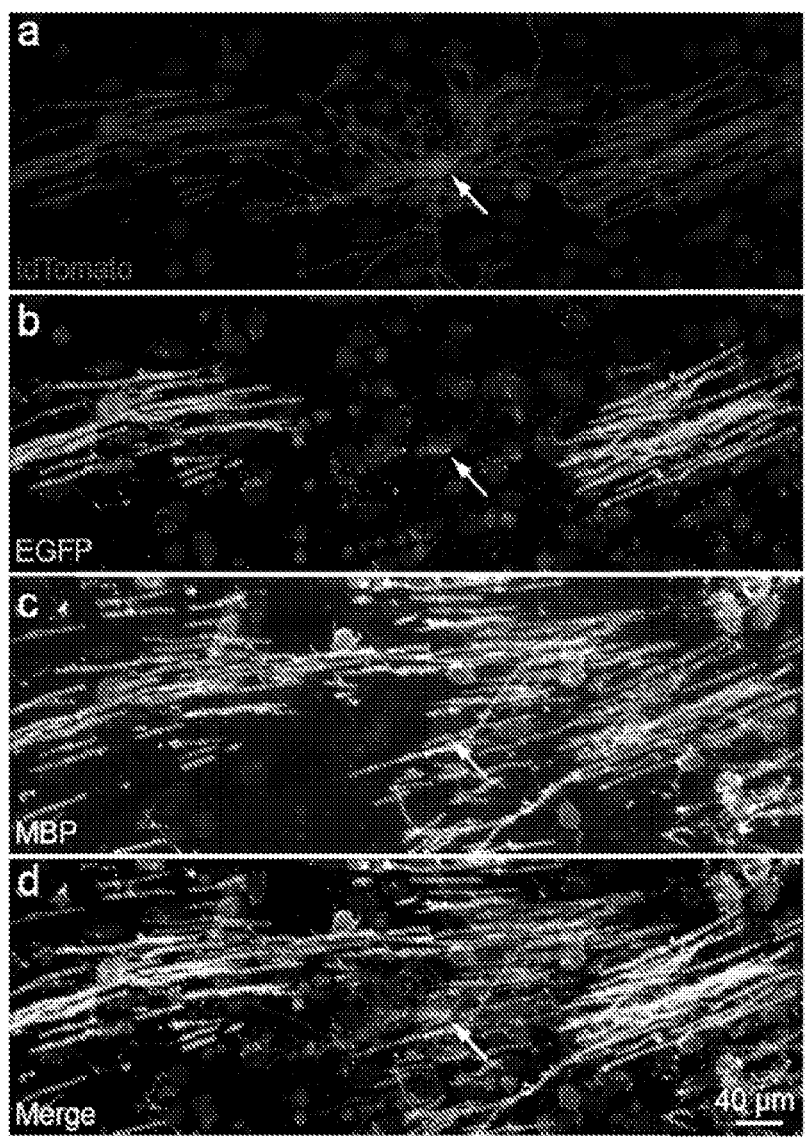
FIGS. 8(*a*)-8(*d*) illustrate the use of dual-fluorescence labeling of oligodendrocyte precursor cells (OPCs) and oligodendrocytes.

The extent and kinetics of myelination has traditionally been difficult to resolve as most screening strategies for myelination cannot be visualized in real time. We will therefore exploit mouse genetics to employ a dual fluorescence labeling strategy using the PLP-creERT2 driver mice in combination with mice expressing memTomato prior to- and memEGFP following cre-mediated recombination (pCA-tdTomato, -EGFP, Jackson). By inducing recombination in oligodendrocytes with tamoxifen, myelination can be visualized and quantified by the expression of memEGFP-positive rings in the absence of memTomato. The screen will be performed in an automated manner under time-lapse microscopy and enclosed in a complete incubation system. The dual-fluorescence labeling strategy will allow for the quantification and resolution to determine effects on the kinetics and extent of myelination. By implementing a dual-fluorescence labeling strategy, we can quantify these processes based on promoter-driven fluorescence intensity and initiate small molecule and biological screens via time-lapse microscopy (FIG. 8). By examining and quantifying the change in fluorescence intensity, we should be able to resolve effects on differentiation and myelination. As a proof of concept, the oligodendroglia from the PLP-creERT2/pCA-tdTomato-EGFP reporter mice proposed in this aim have already been isolated, purified and analyzed in vitro (FIG. 8). The results are consistent with our hypothesis and illustrate the effectiveness of this approach.

FIG. 8. Proof of concept experiment to illustrate the utility of dual-fluorescence labeling of OPCs and oligodendrocytes. (a, b and d) Fluorescence microscopic images of OPCs (Red; Tomato) and oligodendrocytes (Green; EGFP) from PLP/CreERT2XpCA-tdmTomato-mEGFP mice cultured on DRG neurons in the presence of 1 mM tamoxifen for 10 days. Transgenic OPCs were mixed with wildtype OPCs to establish sparse labeling of the oligodendroglia. (c and d) Myelinating oligodendrocytes (white) were identified by immunostaining for MBP. Nuclei (blue) are indicated by DAPI stain. Note an immature OPC (white arrow) is devoid of both EGFP and MBP staining. The EGFP-negative white myelin segments on C and D originate from the wild type oligodendrocytes added to the culture.

The exquisite flexibility and uniformity in the design of our micropillars guarantees a constant and reproducible experimental design. Screening in a 96-well format can be quantified and attributed solely to direct influences on oligodendroglia. By implementing a dual-fluorescence labeling strategy, we can quantify the extent and the kinetics of myelination based on promoter-driven fluorescence intensity and initiate small molecule and biological screens via time-lapse microscopy. This approach will impart valuable insight into the identification of therapeutic molecules and strategies for remyelination in demyelinating conditions.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for screening for candidate agents that promote myelination, the method comprising:
    incubating a candidate agent with a substrate comprising a plurality of micropillars and oligodendrocyte precursor cells (OPCs); and
    determining presence or absence of myelination on the plurality of micropillars by visualization of myelin rings around a circumference of the micropillars,
    wherein the presence of myelination of the plurality of micropillars indicates that the candidate agent promotes myelination,
    wherein the plurality of micropillars comprise micropillars that project vertically from the substrate and comprise a shape that tapers in diameter from a base of the micropillars attached to the substrate to a tip of the micropillars projecting away from the substrate.

2. The method of claim 1, wherein the determining presence or absence of myelination comprises assaying for differentiation of OPCs into oligodendrocytes, wherein the assaying comprises detecting ensheathment of the plurality of micropillars by the oligodendrocytes.

3. The method of claim 1, wherein the determining presence or absence of myelination comprises assaying for concentric wrapping of the plurality of micropillars by oligodendrocytes generated from the OPCs.

4. The method of claim 1, wherein the determining presence or absence of myelination comprises determining a level of myelination.

5. The method of claim 1, wherein the micropillars comprise a base ranging in diameter from 10 μm to 150 μm and a tip ranging in diameter from 0.1 μm to 10 μm.

6. The method of claim 1, wherein the micropillars comprise a height between the tip and the base ranging from 15 μm to 50 μm.

7. The method of claim 1, wherein the shape comprises a conical shape, frusto-conical shape, a bi-conical shape, or a parabolic shape.

8. The method of claim 1, wherein the base ranges in diameter from 25 μm to 50 μm, the tip ranges in diameter from 1 μm to 5 μm, and the height between the tip and the base ranges from 25 μm to 50 μm.

9. The method of claim 1, wherein the shape comprises a conical shape.

10. The method of claim 1, wherein the substrate comprises a plurality of chambers and wherein the plurality of chambers each comprise a plurality of micropillars and the OPCs.

11. The method of claim 10, wherein the incubating comprises incubating a plurality of candidate agents with the substrate comprising the plurality of chambers and the OPCs, wherein the plurality of chambers each comprise a different candidate agent.

12. The method of claim 10, wherein the plurality of chambers each comprise 10 to 200 of the micropillars.

13. The method of claim 10, wherein the shape comprises a conical shape.

14. The method of claim 13, wherein the base ranges in diameter from 25 μm to 50 μm, the tip ranges in diameter from 1 μm to 5 μm, and the height between the tip and the base ranges from 25 μm to 50 μm.

* * * * *